(12) United States Patent
Alberius et al.

(10) Patent No.: US 8,168,095 B2
(45) Date of Patent: May 1, 2012

(54) SPRAY-DRYING PROCESS FOR THE MANUFACTURE OF DYE-LOADED PARTICLES

(75) Inventors: Peter Carl Anders Alberius, Täby (SE); Robert William Corkery, Stockholm (SE)

(73) Assignee: The Procter & Gamble Company, Cincinnati, OH (US)

( * ) Notice: Subject to any disclaimer, the term of this patent is extended or adjusted under 35 U.S.C. 154(b) by 196 days.

(21) Appl. No.: 12/228,373

(22) Filed: Aug. 12, 2008

(65) Prior Publication Data

US 2009/0271932 A1 Nov. 5, 2009

(30) Foreign Application Priority Data

Aug. 13, 2007 (EP) .................................... 07114268

(51) Int. Cl.
*B01J 13/04* (2006.01)
(52) U.S. Cl. .............. 264/4; 264/4.1; 264/4.3; 427/212; 427/213.3; 427/213.31; 427/372.2; 8/523; 8/646; 8/657; 8/653; 8/662; 8/675; 428/402.2
(58) Field of Classification Search ............... 428/402.2; 8/639, 643, 646, 653, 657, 662, 675, 523; 427/213.3, 213.31, 372.2, 212; 264/4, 4.1, 264/4.3
See application file for complete search history.

(56) References Cited

U.S. PATENT DOCUMENTS

| | | | |
|---|---|---|---|
| 4,166,043 A | 8/1979 | Uhlmann | |
| 4,173,491 A | 11/1979 | Abrams | |
| 4,740,443 A | 4/1988 | Nakahara | |
| 4,880,472 A | 11/1989 | Bugnon | |
| 4,894,092 A | 1/1990 | Nishihara | |
| 5,271,769 A | 12/1993 | Bugnon | |
| 5,330,747 A | 7/1994 | Krzysik | |
| 5,382,433 A | 1/1995 | Pahlck | |
| 5,505,937 A | 4/1996 | Castrogiovanni | |
| 5,654,362 A | 8/1997 | Schulz | |
| 5,776,214 A | 7/1998 | Wood | |
| 5,800,816 A | 9/1998 | Brieva | |
| 5,804,298 A | 9/1998 | Moy | |
| 5,880,210 A | 3/1999 | Schulz | |
| 6,238,650 B1 | 5/2001 | Lapidot | |
| 6,303,149 B1 | 10/2001 | Magdassi | |
| 6,387,453 B1 * | 5/2002 | Brinker et al. ................ | 427/387 |
| 7,253,017 B1 | 8/2007 | Roscheisen | |
| 7,524,630 B2 | 4/2009 | Tan | |
| 2005/0265938 A1 | 12/2005 | Cohen | |
| 2005/0276774 A1 | 12/2005 | Elder | |
| 2006/0251687 A1 | 11/2006 | Lapidot | |
| 2007/0292676 A1 | 12/2007 | Naigertsik | |
| 2008/0176263 A1 * | 7/2008 | Schultz et al. .................. | 435/23 |
| 2008/0274148 A1 | 11/2008 | Creeth | |
| 2009/0263658 A1 * | 10/2009 | Alberius et al. ........... | 428/402.2 |
| 2009/0271932 A1 | 11/2009 | Alberius | |
| 2009/0280147 A1 | 11/2009 | Alberius | |

FOREIGN PATENT DOCUMENTS

| | | |
|---|---|---|
| DE | 102005006767 | 8/2006 |
| JP | 60226805 | 11/1985 |
| JP | 4352709 | 12/1992 |
| JP | 5214264 | 8/1993 |
| JP | 2003165921 | 6/2003 |
| WO | WO 02093246 | 11/2002 |
| WO | WO 03060037 | 7/2003 |
| WO | WO 03034979 | 1/2004 |
| WO | WO-2004/081222 | 9/2004 |
| WO | WO 2005115309 | 8/2005 |
| WO | WO 2005118702 | 12/2005 |

OTHER PUBLICATIONS

Mamoru Aizawa et al: "Preparation of Spherical Hydrous Silica Oxide Particles under Acidic Condition via Sol-Gel Processing" Journal of SOL-GEL Science and Technology, Kluwer Academic Publishers, Bo, vol. 19, No. 1-3, 4 pages.
PCT International Search Report, date mailed: Feb. 5, 2009, 4 pages.
Database WPI week 200359, Thomson Scientific, London, GB, AN 3002-627380, XP002493028, 2 pages.
Database WPI week 200427 Thomson Scientific, London, GB, AN 2004-285984, XP002482201, 2 pages.
Database WPI week 199338, Thomson Scientific, London, GB, AN 1993-299810, XP002482202, 1 page.
Database WPI week 198551, Thomson Scientific London, GB, AN 1985-321713, XP002482203, 1 page.
Database EPODOC XP002482200, 2 pages.

* cited by examiner

*Primary Examiner* — Lorna M Douyon
*Assistant Examiner* — Amina Khan
(74) *Attorney, Agent, or Firm* — John G. Powell; Megan C. Hymore

(57) ABSTRACT

According to a first aspect of the invention, a process is provided for the preparation of amorphous particles comprising a homogeneous distribution of one or more dyes encapsulated by an amorphous, siliceous encapsulating agent, the process comprising:
(a) providing a precursor of the encapsulating agent in liquid form;
(b) providing the one or more dyes in liquid form;
(c) mixing the liquid forms;
(d) aerosolizing the mixture to form droplets comprising the one or more dyes and encapsulating agent; and
(e) heating the droplets to form the particles comprising the one or more dyes encapsulated by the siliceous encapsulating agent;
wherein at least one of the liquid forms provided is aqueous and the or each aqueous liquid form is acidic.
According to a second aspect of the invention, encapsulated dyes made by the process of the first aspect of the invention are provided.

10 Claims, 5 Drawing Sheets

SPRAY-DRYING PROCESS FOR THE MANUFACTURE OF DYE-LOADED PARTICLES

FIELD OF THE INVENTION

The present invention relates to a process for the preparation of encapsulated dyes and to encapsulated dyes made by that process.

BACKGROUND TO THE INVENTION

The provision of dyes is key in many fields of technology, for instance in the preparation of cosmetic, personal care and health compositions, detergent compositions and in printing technologies, to name but a few.

Particles incorporating dyes for use in these fields are described in WO-A-2004/081222. This document describes a process for manufacturing encapsulated dyes using the well-known sol-gel methodology, which is an emulsion technique resulting in a core/shell structure (a core of dye surrounded by a shell of a material, such as silica). Further examples of particles of the art are found in US-A-2005/0276774 and US-A-2005/0265938, which describe the production of such particles by dispersive techniques and micelle formation respectively. However, particles made according to the processes described in these documents often exhibit dye leakage, which is clearly undesirable.

Accordingly, there is a need for a new and effective process for the encapsulation of dyes, which results in particles from which there is negligible to no leakage of the dyes over their lifetime.

SUMMARY OF THE INVENTION

According to a first aspect of the invention, a process is provided for the preparation of amorphous particles comprising a homogeneous distribution of one or more dyes encapsulated by an amorphous, siliceous encapsulating agent, the process comprising:
(a) providing a precursor of the encapsulating agent in liquid form;
(b) providing the one or more dyes in liquid form;
(c) mixing the liquid forms;
(d) aerosolizing the mixture to form droplets comprising the one or more dyes and encapsulating agent; and
(e) heating the droplets to form the particles comprising the one or more dyes encapsulated by the siliceous encapsulating agent;
wherein at least one of the liquid forms provided is aqueous and the or each aqueous liquid form is acidic.

According to a second aspect of the invention, encapsulated dyes made by the process of the first aspect of the invention are provided.

BRIEF DESCRIPTION OF THE DRAWINGS

The invention is described with reference to the following drawings, in which.

DETAILED DESCRIPTION OF THE INVENTION

Figure 1A:
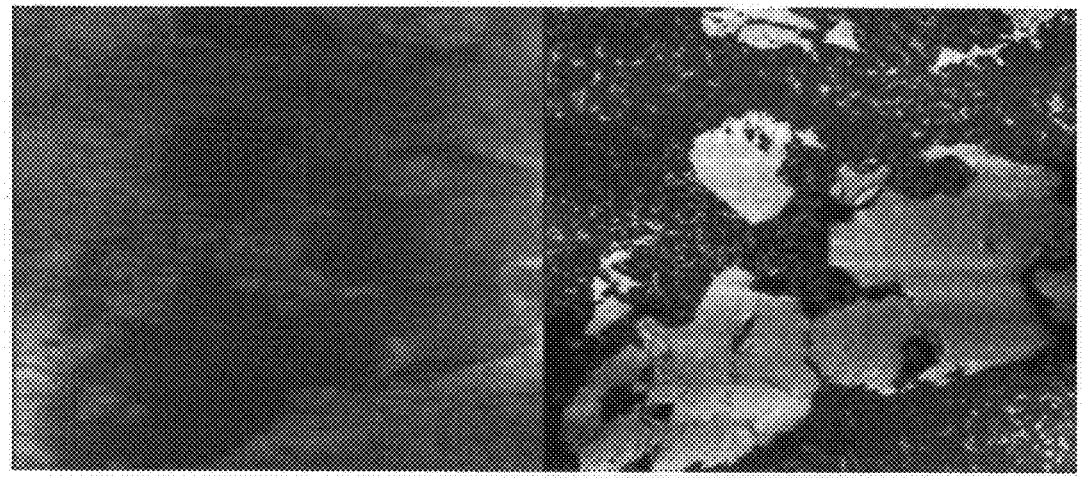
FIGS. 1 (a), (b) and (c) are atomic force microscopy (AFM)images taken at a 2 μm scale, a 500 nm scale and a 100 nm scale respectively with an atomic force microscope in tapping mode on a section cut from the interior of a particle using microtoming and embedded in a standard resin. The particle was made according to the process of the invention.

The dimensions and values disclosed herein are not to be understood to be strictly limited to the exact numerical values recited. Instead, unless otherwise stated, each dimension is intended to mean both the recited value and a functionally equivalent range surrounding that value. For example, a dimension disclosed as "40 mm" is intended to mean "about 40 mm".

In the context of the present invention, the term "encapsulation" is understood to mean that the dye is fully surrounded or encased by an encapsulating agent and, thus, held securely within the particle. Leakage of less than 5 weight %, preferably less than 2 weight %, more preferably less than 1 weight % of the total amount of dye incorporated into the particle is achieved, as determined by the methodology described herein in Example 4.

Both particles and the encapsulating agent comprised within the particles made according to the present invention are amorphous. In the context of the invention, the term "amorphous" means that there is no long range crystallographic order in one, two or three dimensions at lengths from 0.1-50 nm, as determined in the following way by a combination of powder x-ray diffraction (XRD) on bulk samples and transmission electron microscopy (TEM) of representative portions of the same bulk sample:
  (a) The presence of a broad peak in the x-ray diffractogram centered between 2 theta angles corresponding to d-spacings of 0.37-0.42 nm, with full width half-maximum (FWHM) of between 5-10 degrees 2 theta;
  (b) The lack of sharp powder x-ray diffraction peaks corresponding to spacings of crystallographic planes separated by 0.37-0.42 nm;
  (c) The lack of mesocrystalline order (where respective highest order Bragg peaks fall in the range 2-50 nm—typical of ordered mesostructured materials), as determined by TEM imaging of samples prepared by microtoming;
  (d) The lack of a multiplicity of sharp peaks in the range of two theta angles corresponding to d-spacings to 0.1-50 nm.

This definition excludes ordered mesoporous materials with pore sizes from 2-50 nm arranged with translational crystallographic order, such as MCM-41, MCM-48 and SBA-15.

In the context of the present invention, the term "siliceous" takes its normal meaning known in the art. More specifically, a siliceous material is one of, relating to or containing silica or a silicate. Preferably, the encapsulating agent is silica per se. Optionally, however, a proportion of the silicon within the amorphous silica structure may be substituted with other elements such as boron, lead, titanium, tin, zirconium and/or aluminium. This substitution of the silica framework may be useful in adjusting the properties of the silica-based particles depending upon their specific applications. For example, addition of boron, lead, tin, zirconium and/or aluminium may result in a different refractive index.

The process of the invention is a spray-drying, or aerosol method for the preparation of amorphous particles comprising a homogeneous distribution of one or more dyes encapsulated by an amorphous, siliceous encapsulating agent.

This process comprises the step of providing a precursor of the encapsulating agent in liquid form. The liquid form of the encapsulating agent may be a solution, a suspension or a dispersion, and is preferably a solution. The liquid form of the encapsulating agent typically comprises at least one source or precursor of the siliceous encapsulating agent per se which, during the aerosol process, ultimately provides the desired siliceous encapsulating agent. The source of encapsulating agent may be considered to be a pre-polymer as, during aerosolisation, it will polymerise or crosslink to form the desired siliceous encapsulating agent. Preferably the siliceous precursor is organic. Suitable sources or precursors which may be used in the aerosol process to form particles of the invention include all those conventionally used in the art to form silica, silicates and zeolites, for example. Specific examples of useful silica precursors include tetramethylorthosilicate (TMOS), tetraethylorthosilicate (TEOS), tetrapropylorthosilicate (TPOS), tetraisopropylorthosilicate (TiPOS), tetrabutylorthosilicate (TBOS), silicic acid which may for example be modified with cations such as sodium or ammonium so that it is provided in the form of sodium silicate (also known as waterglass) or ammonium silicate. TEOS is a particularly preferred source of silica from a safety perspective, because the by-product of the process is ethanol (not methanol, as is the case for TMOS).

As is easily determinable and generally known by a skilled person, approximately one third of the weight of precursor is transformed into particles. For example, silica ($SiO_2$) has a molecular weight of 60 g/mole and TEOS has a molecular weight of 208 g/mole, so the weight of silica produced is 60/208 or 0.29 times the amount of TEOS. For TMOS the value is 0.39 (the molecular weight of TMOS is 152 g/mole).

In the event that the liquid form of the precursor of the encapsulating agent is a solution, then a solvent will need to be employed and the solvent used will depend upon the hydrophobicity of the starting material. TEOS, TMOS and TPOS are hydrophobic and are therefore generally solubilised in an essentially non-aqueous material, for example as an alcoholic solution such as a solution in ethanol, methanol, n-propanol, iso-propanol and/or a butanol, ie. n-butanol, 2-butanol, iso-butanol or tert-butanol. Alternatively, a solution in acetone or one or more other conventional solvents, for instance, may also be employed. Silicic acid and the silicates are hydrophilic so may be dissolved in hydrophilic solvents such as water. The amounts of solvent used are readily determinable by a skilled person—the lower limit is, in practice, determined by the solubility parameters of the starting material and the upper limit is a practical one—the more solvent one uses, the smaller the final particles and the smaller the production capacity.

Although the solvent may be non-aqueous, some water is, nevertheless, necessary in order to hydrolyse the precursor, such as TEOS, to silicic acid prior to aerosolisation. Hydrolysis prior to aerosolisation is important to minimise the number of pores in then resulting particles, thereby minimising leakage of encapsulated dye. As discussed below, it is usually preferred that the liquid form of the dye be an aqueous solution and this aqueous solution usually acts as the source of water for hydrolysis of the precursor. However, it is also possible that water be included with the liquid form of the precursor as well, especially if, as discussed above, the precursor is hydrophilic. If water is present in the liquid form of the precursor, then it is preferred that the aqueous portion be an acidic solution. The pH is more than 1 and less than 7, is preferably more than 1 and less than or equal to 4, more preferably 1.5 or more and less than or equal to 2.5 and is advantageously approximately 2, as this is at or near the iso-electric point of silica itself. The pH of the precursor liquid form may be adjusted as desired using techniques conventionally used in the art, for example by addition of acid. A preferred acid used for this purpose is hydrochloric acid. Water of the requisite pH may be introduced as a solvent for the silica precursor or as a solvent for the dye, as discussed below.

Turning now to the dyes included in the particles of the invention, the process according to the invention comprises the step of providing a precursor of the one or more dye(s) in liquid form. The liquid form of the one or more dye(s) may be a solution, a suspension or a dispersion, and is preferably a solution.

A wide variety of dyes is suitable for this purpose. In the context of the present invention, the term "dye" refers to any dye or colorant, which is desired to be introduced into a particle and indefinitely retained within that particle. Examples of dyes which may be comprised within particles of the present invention include, but are not limited to, dyes or colorants conventionally used in the end application(s) of choice. For example, the suitability of dyes for use in applications such as cosmetic, health, personal care and detergent compositions is governed by organisations such as the Food and Drug Administration (FDA) in the USA and equivalent bodies in other countries. Typically, dyes suitable for use in the present invention may be cationic, anionic, neutral, amphoteric, zwitterionic or amphiphilic, with cationic dyes being preferred, as the positive charge on the dye molecule interacts with residual negative charge on the siliceous encapsulating agent to promote retention of the dye within the encapsulant. The dyes are typically selected from conventionally-known dye types such as natural dyes, ie. those derived from natural sources or synthetic equivalents thereof, azo dyes, indigoid dyes, triaryl-methane dyes, anthraquinone dyes, xanthine (xanthene) dyes, nitrosulphonate dyes, pyrene dyes, thiophene dyes, quinoline dyes and derivatives, lakes, composites or mixtures thereof, in particular those which have been approved for use by the FDA. Examples of suitable dyes are provided in the following tables (1 and 2), with their general dye types shown in brackets.

TABLE 1
| | Colour Additives batch-certified by the FDA | |
|---|---|---|
| Standard Name | Chemical Structure | Colour Index Number (CI) |
| FD&C Black No. 2 | Carbon black | 77266 |
| FD&C Orange No. 4 (monoazo) | 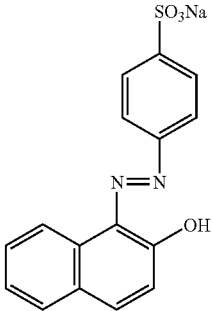 | 15510 |
| FD&C Orange No. 5 (xanthene-based) | 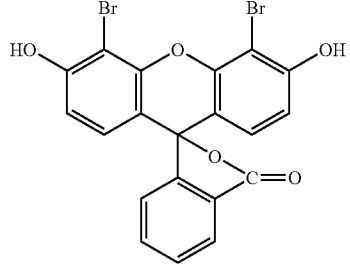 | 45370 |
| FD&C Orange No. 10 (xanthene-based) | 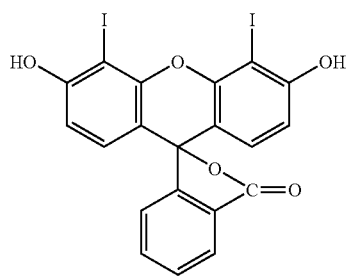 | 45425 |
| FD&C Orange No. 11 (Sodium salt of Orange No. 10; xanthene-based) | 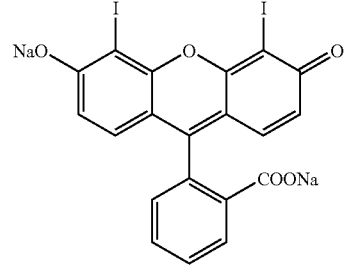 | 45425 |

TABLE 1-continued

Colour Additives batch-certified by the FDA

| Standard Name | Chemical Structure | Colour Index Number (CI) |
|---|---|---|
| FD&C Blue No. 1 (triarylmethane; "Erioglaucine") | [structure] | 42090 |
| FD&C Blue No. 4 (triarylmethane) | [structure] | 42090 |
| FD&C Brown No. 1 (diazo) | [structure] | 20170 |

TABLE 1-continued

Colour Additives batch-certified by the FDA

| Standard Name | Chemical Structure | Colour Index Number (CI) |
| --- | --- | --- |
| FD&C Violet No. 2 (anthracene dione-based; ie. anthraquinone based) | *[structure: 1-(p-tolylamino)-4-hydroxyanthraquinone]* | 60725 |
| Ext. D&C Violet No. 2 (anthracene-based) | *[structure: 1-((2-sulfo-4-methylphenyl)amino)-4-hydroxyanthraquinone, sodium salt]* | 60730 |
| FD&C Green No. 3 (triarylmethane) | *[structure: triarylmethane dye with OH, SO₃⁻, and two N-ethyl-N-benzylsulfonate amino groups]* | 42053 |

TABLE 1-continued

Colour Additives batch-certified by the FDA

| Standard Name | Chemical Structure | Colour Index Number (CI) |
|---|---|---|
| FD&C Green No. 5 (anthracene-based) | 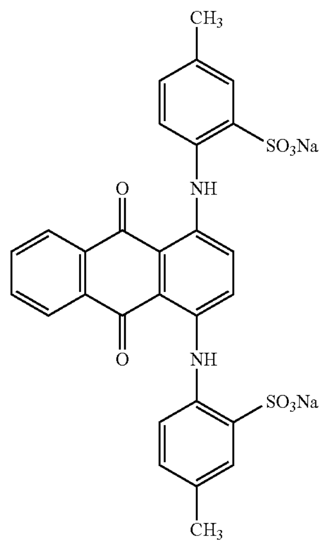 | 61570 |
| FD&C Green No. 6 (anthracene-based) | 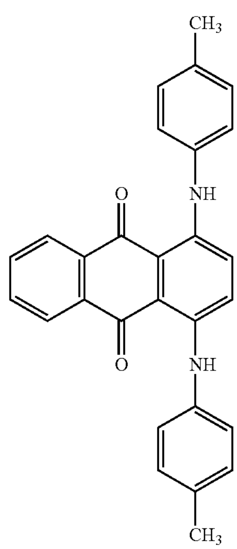 | 61565 |
| FD&C Green No. 8 (pyrene-based) | 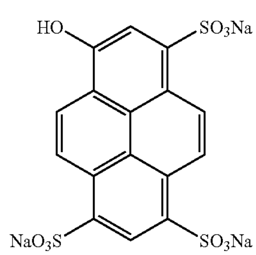 | 59040 |

TABLE 1-continued
Colour Additives batch-certified by the FDA
| Standard Name | Chemical Structure | Colour Index Number (CI) |
|---|---|---|
| FD&C Red No. 2 (monoazo; "Amaranth") | 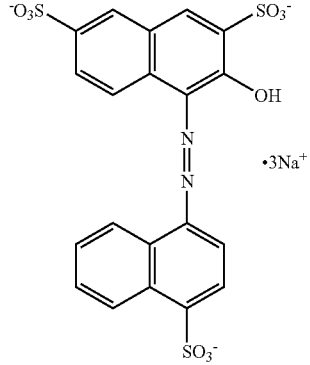 | 16185 |
| FD&C Red No. 4 (monoazo) | 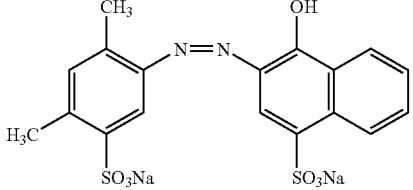 | 14700 |
| FD&C Red No. 6 (monoazo) | 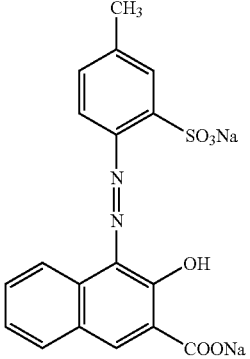 | 15850 |
| FD&C Red No. 7 (monoazo) | 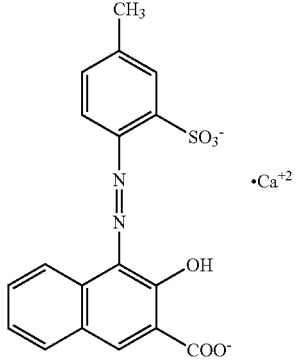 | 15850 |

TABLE 1-continued

Colour Additives batch-certified by the FDA

| Standard Name | Chemical Structure | Colour Index Number (CI) |
| --- | --- | --- |
| FD&C Red No. 17 (diazo) | 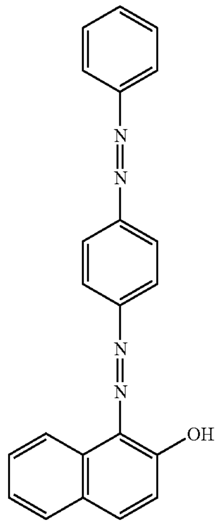 | 26100 |
| FD&C Red No. 21 (xanthene-based) | 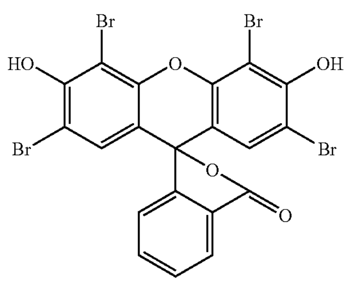 | 45380 |
| FD&C Red No. 22 (xanthene-based) | 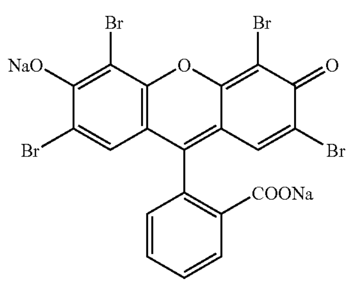 | 45380 |
| FD&C Red No. 27 (fluoran based) | 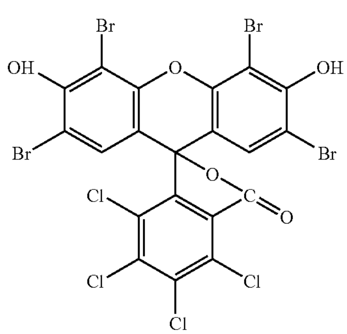 | 45410 |

TABLE 1-continued

Colour Additives batch-certified by the FDA

| Standard Name | Chemical Structure | Colour Index Number (CI) |
|---|---|---|
| FD&C Red No. 28 (xanthene-based) | 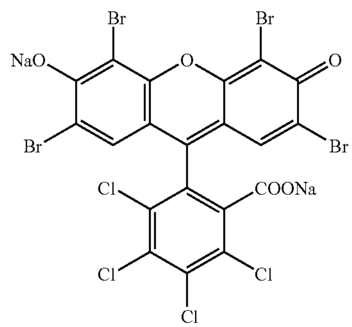 | 45410 |
| FD&C Red No. 30 (indigoid) | 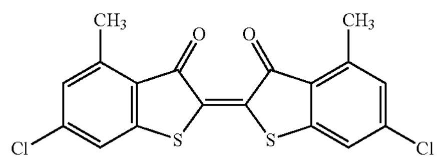 | 73360 |
| FD&C Red No. 31 (monoazo) | 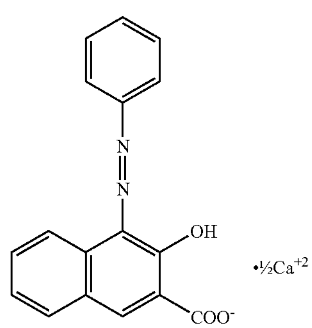 | 15800 |
| FD&C Red No. 33 (monoazo) | 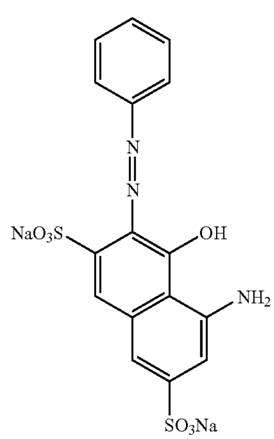 | 17200 |

TABLE 1-continued

Colour Additives batch-certified by the FDA

| Standard Name | Chemical Structure | Colour Index Number (CI) |
|---|---|---|
| FD&C Red No. 34 (monoazo) | (structure with naphthalene-$SO_3^-$, N=N, OH, COO$^-$, ·Ca$^{+2}$) | 15880 |
| FD&C Red No. 40 (monoazo) | (structure with $H_3C$, $SO_3Na$, $OCH_3$, N=N, OH, $NaO_3S$) | 16035 |
| FD&C Yellow No. 5 (monoazo; "Tartrazine") | (structure with $NaO_3S$, N=N, COONa, HO, N, N, $SO_3Na$) | 19140 |
| FD&C Yellow No. 6 (monoazo) | (structure with $SO_3Na$, N=N, OH, $NaO_3S$) | 15985 |

TABLE 1-continued

Colour Additives batch-certified by the FDA

| Standard Name | Chemical Structure | Colour Index Number (CI) |
|---|---|---|
| FD&C Yellow No. 7 (xanthene-based) | 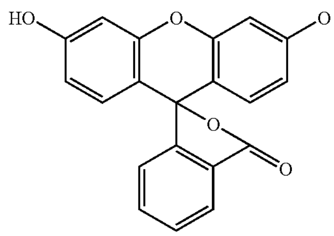 | 45350 |
| Ext. D&C Yellow No. 7 (dinitroarylsulphonate) | 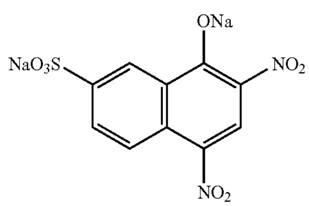 | 10316 |
| FD&C Yellow No. 8 (xanthene-based) | 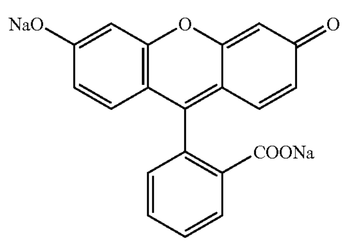 | 45350 |
| FD&C Yellow No. 10 (quinoline-based) | 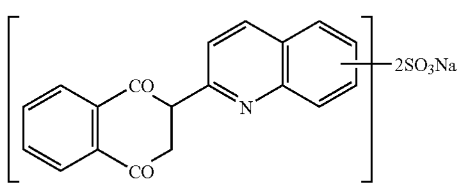 | 47005 |
| FD&C Yellow No. 11 (quinoline-based) | 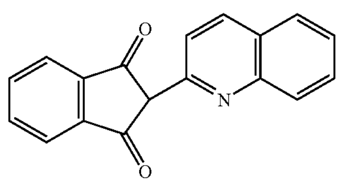 | 47000 |

TABLE 2

Natural Colour Additives which are Exempt from Batch Certification by the FDA

| Name | Structure | CI |
|---|---|---|
| Caramel | Not applicable (n//a) | |
| Cochineal | 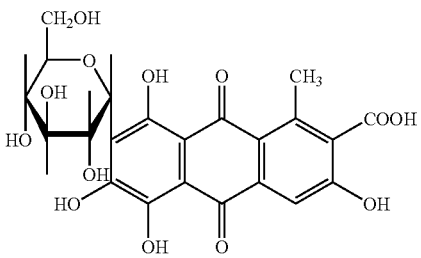 | 75470 |
| Beta carotene | 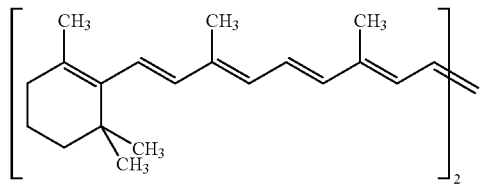 | 40800 or 75130 |
| Guanine | 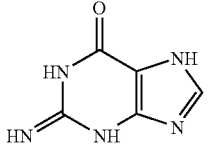 | 75170 |
| Henna | n/a | n/a |

The dye may be used in an unadulterated form or it may be adapted to improve its suitability to the present process. In particular, the effectiveness of some dyes containing anionic groups and a mono-valent alkali metal counter-ion, such as sodium, may be improved by ion-exchanging the metal ion with a mono-valent organic counter-ion such as ammonium or tetra-methyl ammonium.

Particularly preferred colorants or dyes include xanthene, triarylmethane, anthracene, and monoazo dyes.

As discussed above, the liquid form of the one or more dyes is preferably a solution. The solution is formed in one or more solvents conventionally used in this field, preferably water or an alcohol such as methanol, ethanol, n-propanol, iso-propanol or a butanol, and is more preferably ethanol or water.

As mentioned above, it is desirable that, in creating the aerosol to form the particles of the invention, at least one of the liquid forms of encapsulating agent and dye should be aqueous. It is usually preferred that the dye be provided in aqueous liquid form, whereas the siliceous precursor is typically provided in non-aqueous form. The presence of water in the reaction medium aids pre-hydrolysis of the silica precursor which, in turn, aids subsequent polymerisation of the precursor to form the desired encapsulating agent comprising a low number of pores. The liquid forms of the dye and precursor are mixed together prior to entry into the aerosol chamber for this purpose.

Highly preferably, the dye is provided in the form of an aqueous solution, and conveniently as an aqueous solution comprising ethanol. It may be necessary to aid dissolution of the active in the chosen solvent by providing it in the form of a salt, for instance those formed with commonly-used cations such as sodium, ammonium or potassium, or by adjusting the pH of the mixture of dye and solvent, again by conventional methods as previously described.

The solution of the one or more dyes employed in the process of the invention is in acidic form. The pH is more than 1 and less than 7, is preferably more than 1 and less than or equal to 4, more preferably 1.5 or more and less than or equal to 2.5 and is advantageously approximately 2, as this is at or near the iso-electric point of silica itself. The pH of the precursor liquid form may be adjusted as desired using techniques conventionally used in the art, for example by addition of acid. A preferred acid used for this purpose is hydrochloric acid.

The amount of dye included in the liquid form of the dye will depend on the amount of dye desired in the particles of the invention and can be varied in accordance with the desired applications or effects of the particles and may also depend upon the type(s) of dye chosen to be included within the particles. Particles made according to the process of the invention generally comprise more than 0 and up to 25%, preferably from 3% to 20%, more preferably from 5% to 15%, and more preferably still from 8 to 12% of dye by weight of the particle. These ranges have been found to equate exactly to the percentages of the starting materials used in the process of the invention to make the particles.

The amount of dye to be encapsulated within the particles of the invention is easily calculable by a skilled person. For example, if one wants a 10% dye loading, then, bearing in mind how much precursor one needs, as discussed above, it is a straightforward matter to calculate the amount of dye needed (a precursor solution of 10.4 g of TEOS and 0.33 g of dye, for example, yields silica particles comprising 90% silica (3 g silica) and 10% dye (0.33 g dye)).

According to the process of the invention, the liquid forms of encapsulating agent precursor and dye are mixed prior to aerosolisation. Mixing may be effected using any appropriate mixing unit operation, as determined by the skilled person.

Aerosolisation may be performed under temperature, pressure and other conditions as desired by the skilled person in this technical field. Typically and conveniently, however, aerosolisation is performed under ambient temperature and pressure conditions, ie. at room temperature of approximately 18-25° C., and at a pressure of approximately atmospheric pressure. However, it will be appreciated that lower or higher temperatures and pressures may be employed as desired. In addition, although not essential to exclude humidity from the aerosol apparatus, the relative humidity (RH) within the aerosol apparatus under ambient conditions, is typically less than 50%, as measured by conventional techniques.

The droplets formed in the spray chamber are typically held in the chamber for a residence time in the range of greater than 0 up to about three minutes. Residence time may affect the porosity and, to a limited extent, the size of the resulting particles. For instance, for an average particle size of approximately 3-5 µm and a minimum porosity, a residence time of approximately 10 seconds may be conveniently employed. When present in the spray chamber, the encapsulating agent undergoes crosslinking within itself, thus forming droplets of a secure cage-like structure or network within which the dye is securely held. In addition, of course, the solvents evaporate. Typically the particles according to the invention have a diameter which is half that of the droplets sprayed into the spray chamber.

Following aerosolisation and concomittant droplet formation, the droplets are heated to effect condensation and crosslinking of the siliceous encapsulating agent to give rise to substantially fully crosslinked polymer-encapsulated dye particles. Heating may be effected using any appropriate heating unit operation, as determined by the skilled person. Typically, a temperature in the range of 100° C.-300° C. and preferably in the range 140° C.-260° C. is employed.

Optionally, the particles may undergo a subsequent washing process, in order to ensure that all of the dye is securely encapsulated within the particles and that none remains at the surface of the particles following the process of the invention, for example. Conventional washing agents or solvents such as water, alcohols or acetone may be used for this purpose, the choice of washing agent typically being dependent upon the solubility characteristics of the relevant dye(s).

Figure 2:
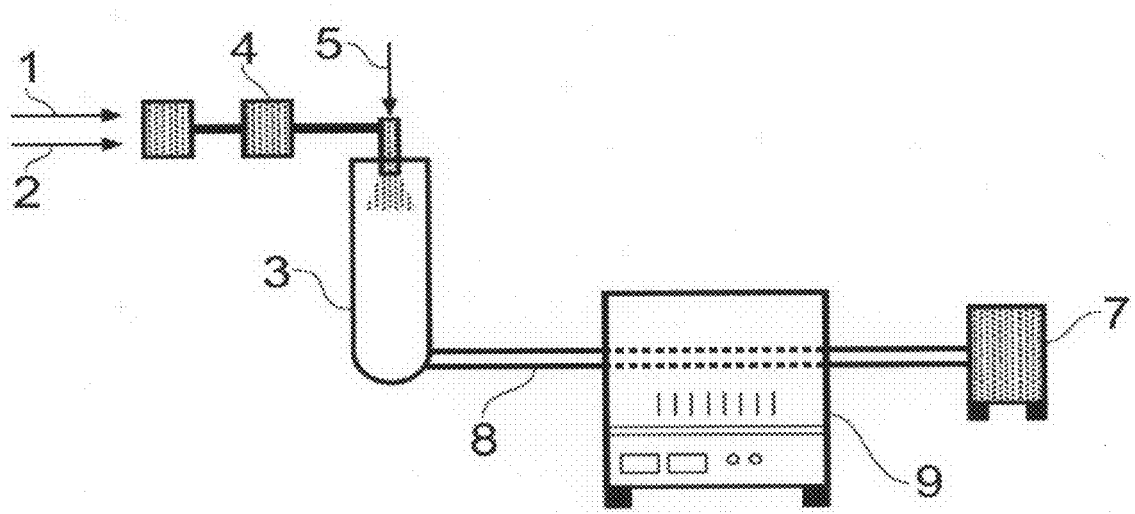
FIG. 2 is a schematic representation of an apparatus suitable for use in the process of the invention.

A suitable aerosol procedure is described with reference to FIG. 2 in which the encapsulating agent (1) and dye (2) are mixed, then introduced in liquid form into a spray chamber (3), generally via means of a pump (4), together with a carrier gas (5) which is typically an inert gas such as nitrogen, or air dried by conventional methods for example.

Figure 3:
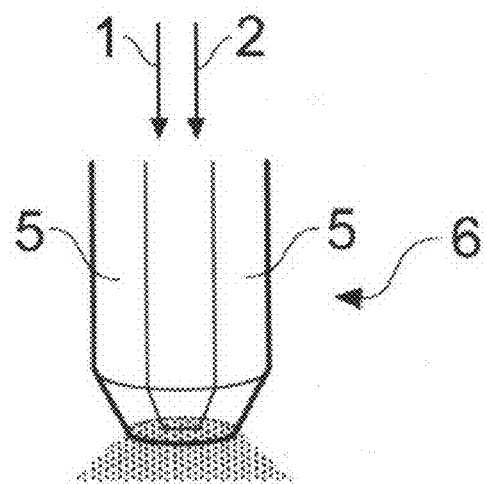
FIG. 3 is a schematic representation of the nozzle used in the apparatus shown in FIG. 2.

Typically a spray nozzle (6) such as that shown in FIG. 3 is used in the aerosol process, whereby the dye (2) and agent (1) are introduced through a central tube and the carrier gas is introduced through an outer tube of the nozzle. This type of nozzle is conventionally known as a "two-flow spray nozzle", however, other nozzle types commonly used in creating aerosols may also be employed. A two flow nozzle is preferred as the carrier gas flow cuts across or dissects the central flow of dye and encapsulating agent, thus facilitating more effective formation of spray droplets comprising the encapsulating agent and dye. Whilst the apparatus shown in FIG. 3 illustrates a downwardly-spraying nozzle, it will be appreciated that all conventional types of aerosol apparatus including upwardly spraying apparatus may be conveniently used in the aerosol process. Indeed, so-called "spray up" systems may be preferred where it is desirable to fractionate particles of different sizes directly from the spray chamber, for instance.

The droplets are then removed from the spray chamber in a conventional manner for instance via means of a pressure differential created by a pump (7) located at the end of a tube (8), into which the droplets pass from the spray chamber. Generally, the tube (8) into which the droplets pass is heated to a temperature which will effect drying of the particles for instance via means of a heater (9). Typically, a temperature in the range of approximately 140-260° C. is employed. Heating of the droplets in this way promotes condensation and, thus, further crosslinking of the siliceous encapsulating agent, preferably ultimately resulting in the formation of substantially fully crosslinked polymer-encapsulated dye particles.

The particles made in the aerosol process are typically dried by any means conventionally known in the art, such as a heater, either before or after their recovery from the aerosol apparatus which is, again, achieved in a conventional manner.

Depending upon the desired applications and/or effects of the particles made according to the process of the invention, it may be desirable for them to additionally comprise one or more inorganic particles, such that they comprise not only the siliceous encapsulating agent and one or more dyes, but also discrete inorganic particles such as titanium dioxide, zinc oxide, aluminium oxide and mixtures thereof, within their structure. For instance, titanium oxide and zinc oxide may provide additional sunscreen benefits. Such additional particles preferably have a mass average particle size of less than about 1 µm, preferably less than 100 nm. If the siliceous encapsulating agent incorporates other inorganic materials in its structure in addition to silica, these may also be provided to the aerosol process in liquid forms of conventional sources of such materials. If it is desired to include titanium dioxide, for example, it may be appropriate to include a solution tetraethoxytitanate dissolved in an appropriate solvent, such as ethanol.

With reference to the particles made according to the process of the invention, the dye molecules are typically present within the particle in more than one area or "pocket". This beneficially maximises the dye to particle volume or weight ratio and, thus, maximises the amount of dye ultimately included in the desired end compositions, for example the cosmetic, health, beauty or detergent products or ink compositions, whilst minimising the overall proportion of dye particles within such compositions. Irrespective of the number of areas or "pockets" of dye within the particle, each is fully surrounded or encapsulated by the encapsulating agent and, thus, held securely therein. Therefore, within the structure of the particles themselves, the encapsulating agent may be thought of as a continuous phase or matrix, whereas the dye may be thought of as comprised within a discontinuous phase. It follows that an "encapsulating agent" is an agent, which may be used to achieve this effect.

In this respect, the encapsulating agent may also be considered to be polymeric in nature because it will tend to possess crosslinking within its structure. It is preferred that the particles made according to the process of the invention have as high a degree of crosslinking as possible, such that the dye is most effectively retained within the resulting particle and cannot leach therefrom. The degree of crosslinking may be observed using standard techniques such as Fourier transform infrared spectroscopy (FTIR) or solid state nuclear magnetic resonance spectroscopy (solid state NMR). Ideally and as previously mentioned, leakage of less than 5 weight %, preferably less than 2 weight %, more preferably less than 1 weight % of the total amount of dye incorporated into the particle is achieved, as determined by the methodology described herein in Example 4.

Additionally, the particles of the invention comprise a homogeneous distribution of the one or more dyes within the encapsulating agent. In the context of the present invention, this "homogeneous distribution" of the dye is understood to mean that the dye is homogeneously dispersed throughout the particle on a "molecular level". This means that the dye, typically present in one or more areas or "pockets", is not visible or discernible via microscopic techniques down to a range or magnification of 2 nm. In other words, the particles of the invention appear as a homogeneous or single material at this level of microscopic magnification. This is illustrated by the AFM images shown FIG. 1, which were taken with an atomic force microscope in tapping mode on a section cut from the interior of a particle using microtoming and embedded within a resin. The particle of the invention investigated by this technique was that of Example 1 herein.

Figure 1B:
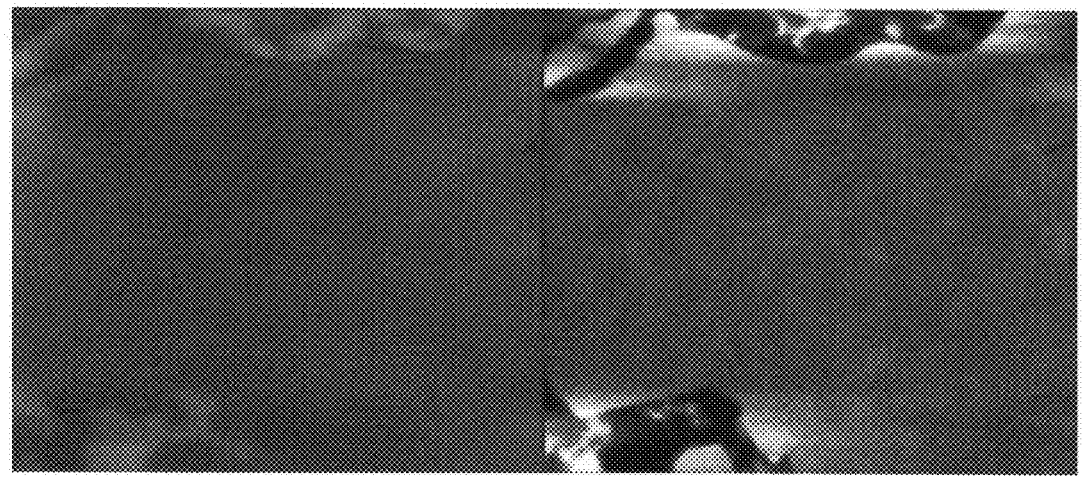
Figure 1C:
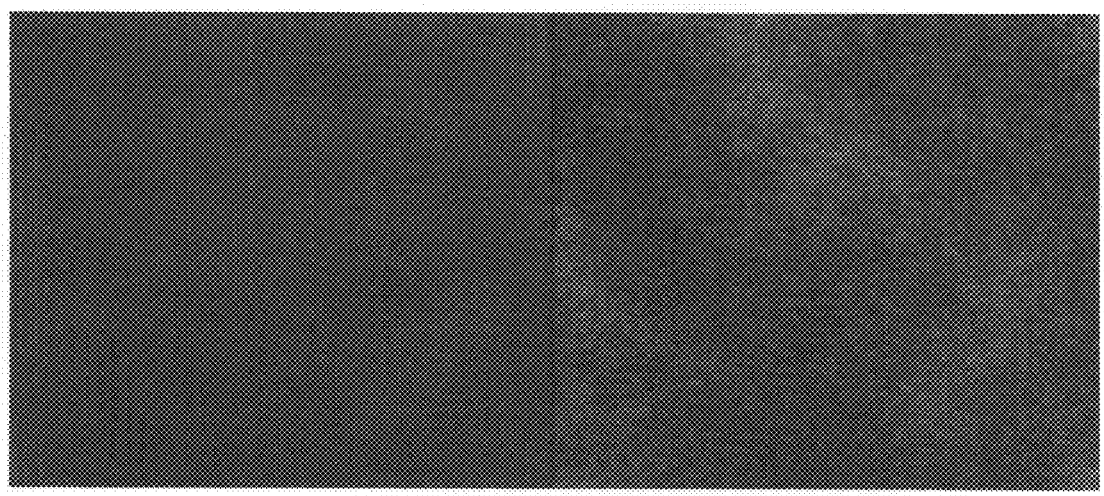

The AFM image on the left hand side of FIG. 1 (a)-(c) shows the variation within the particle in terms of its height, whereas the AFM image shown on the right hand side of FIG. 1 shows the variation in phase within the particle. Each of the images shows that the composition of the particle is essentially homogeneous over this area range and, indeed, down to a range of at least 2 nm, ie. "at a molecular level". The phase image on the right hand side of FIG. 1(a)-(c) essentially records an image based upon the differential hardness of the particle sample. From the phase image, it may in fact be concluded that the particle is uniformly textured almost to the resolution limit of the highest magnification image. Accordingly, it may be concluded that any encapsulating agent cages or pockets, within which the dye molecules are held, must therefore be in the range of less than approximately 2 nm in average diameter or size. Furthermore, the AFM images do not identify any regions of dye aggregates, which would appear softer and a different colour in the phase image. Therefore, the AFM results appear to show that the dye molecules are homogeneously distributed in pockets or cages within the silica network.

Without wishing to be bound by theory, therefore, the compositional homogeneity of the particles, as shown particularly well by the AFM images in FIG. 1 (a)-(c), appears to be key to the retention of the dye within the particles. This homogeneity has not been seen with particles of the prior art.

The particles of the invention have a volume average particle size which renders them useful in the end application of choice. For instance, if the particles are to be used in cosmetic or beauty formulations, it is desirable that they are not discernible to the naked eye. Thus, such particles will typically have an average size of less that about 70 µm. However, if the particles are destined for used in detergent or other formulations, they may have greater sizes, for example. For cosmetic applications, the average particle size is generally in the range of greater than 0 to 10 µm, preferably in the range of greater than 0 to 5 µm, more preferably from greater than 0 to less than 1 µm and even more preferably, is from 10 nm to less than 1 µm. The average particle size of the particles is measured using standard techniques of the art, such as light scattering via use of a Malvern Sizer 2000 apparatus or by scanning electron microscopy (SEM).

The particles of the invention may have any shape appropriate to the end use in question. Preferably, the particles according to the invention are spherical because such particles may have more predictable qualities, such as optical and rheological properties. Within a cosmetic application, spherical particles may also provide improved skin feel, since they may act as a lubricant by providing a ball-bearing type effect.

The particles of the invention achieve effective retention of dyes therein by an amorphous, siliceous encapsulating agent. The invention provides particles which possess good chemical and physical stability, colour fastness and tint strength as well as an acceptable environmental profile. A corollary of the low dye leakage is that the surface of the silica encapsulates according to the present invention has similar properties to silica per se, regardless of the dye(s) incorporated therein. Thus, the particles may be reliably and effectively incorporated into compositions for use in a wide variety of applications to provide colorants, which show negligible to no leakage from the compositions into which they are incorporated and which, at the same time, provide more robust coloration to the compositions than colorants of the art. Because of this, the particles of the invention may be effectively used to provide previously unattainable dye combinations, as the individual dyes are securely held in the inventive particles.

In addition, the dye particles of the invention may be formulated into bulk colorant compositions for convenient "drop-in" use in the desired end compositions. This is particularly advantageous as end compositions currently formulated typically require specific, tailored formulation of all their individual components, including their colorants, in order to provide the correctly formulated end composition. Thus, use of colorant particles of the present invention obviates the need for this repetitive, time-consuming and, therefore, uneconomic "custom" formulation by enabling the formulation of bulk end-product compositions which may then be coloured as desired using bulk colorant compositions comprising pre-determined proportions of dye particles made by the present invention.

Particles according to the present invention have a specific surface area of 0.1 $m^2/g$ to 25 $m^2/g$, preferably 0.5 $m^2/g$ to 5 $m^2/g$, more preferably 0.5 $m^2/g$ to 3.5 $m^2/g$. In addition, particles according to the present invention have a specific internal pore volume of 0.001 to 0.03 $cm^3/g$, preferably 0.001 $m^3/g$ to 0.011 $cm^3/g$. Surface areas and pore volumes are determined using nitrogen porosimetry using nitrogen at a temperature of −196° C. or 77K. The samples are evacuated at 120-150° C. for at least 4-6 hours to remove adsorbed water from the pores, and sample sizes are preferred to be around 0.5 g. Otherwise standard procedures for collecting high quality $N_2$ isotherm data should be followed. The pore volumes are cumulative pore volumes for internal pores less than 50 nm in diameter and are determined using the "Barret-Joiner-Halenda" method.

EXAMPLES

The present invention will now be described in more detail with reference to the following non-limiting example(s):

Example 1

Preparation of Silica loaded with Tartrazine (FD&C Yellow No. 5)

As a first step to synthesising sodium tartrazine-containing silica, the dye (commercially available from Sigma as T0388-100G (CAS# 1934-21-0) was ion-exchanged using a column with ion-exchanging resin (type Dowex 50Wx8 commercially available Dow Chemical Comp., Michigan, USA. This was necessary because the use of commercial Tartrazine induces flocculation of the tetraethylorthosilicate/ethanol/hydrochloric acid (TEOS/EtOH/HCl) encapsulating agent mixture.

Column Preparation

The column was loaded with 317 g Dowex 50Wx8 to obtain a 400 ml bed volume.

Step 1—Washing: to remove residual sodium cations, the column was eluted with 2.5 l deionized water over 5 to 10 minutes at pH 6.

Step 2—Reconditioning: to remove bound sodium cations the column was washed through with four batches of 400 ml 7% HCl. The contact time of HCl on the column was 45 minutes.

Step 3—Washing: as for Step 1.

Step 4—Charging: as for Step 2, but it was performed using 7% ammonium chloride ($NH_4Cl$) instead of HCl.

Step 5—Washing: as for Step 1, the purpose being to remove excess ammonium cations.

Ion Exchange of Dye

A 10% dye solution of sodium tartrazine was prepared in an acidic solution of water and ethanol and was eluted through the column. This solution was used to produce Tartrazine-containing silica in the subsequent procedure.

Spraying of Silica with Yellow Dye

Two batches of coloured silica were each prepared using 10.4 g TEOS, 5.4 g of HCl with a pH of around 1.25 and 12.0 g of ethanol. The components were mixed together and the mixture was left stirring for 30 minutes. Theoretically, such a mixture should give 3 g of silica after aerosolisation. The calculation of the amount of Tartrazine solution to add was based on this theoretical amount of silica. The ion-exchanged Tartrazine solution was then mixed with 4 g of ethanol.

The two resulting mixtures were then blended together, the pH was adjusted to pH 2.0 using 1M HCl and the blend was left under stirring for a further 10 minutes. The blend was then aerosolized and spray-dried as follows:

The starting solution blend is pumped at a constant rate of 3 ml/minute using a peristaltic pump to the centre flow outlet of a coaxial two-flow spray nozzle of a spray tower. At the same time, compressed air is pumped at 20 litres/minute (at STP) to outer annular outlet located coaxially around the centre flow outlet. The centre flow outlet diameter is 1 mm; the outer diameter is 1.5 mm. The spraying was such that a turbulent mixture was propelled into the spray chamber, which was retained at ambient temperature. Afterwards, the mixture was heated to 220° C. to induce cross-linking and drying of the particles.

Washing of Particles

The particles were washed with de-ionized water, at a rate of 200 ml water per 1 g of particles as follows: 5 g of particles were placed into a plastic bottle and 1000 ml of water were added. The mixture was left under stirring for 5 minutes and it was then centrifuged for 10 minutes at 3500 rpm. The sediment was then separated from the supernatant fluid.

Separation of Small Particles

The sediment from the centrifuged mixture was mixed with 1000 ml water in a beaker and left to settle for two days. The resulting supernatant fluid was then pumped into another beaker using a roll pump. Once the supernatant had been pumped into the other beaker, it was centrifuged at 3500 rpm for 20 minutes and the resulting sediment was separated using a standard separation technique from the liquid. The resulting particles were then dried in an oven at 50° C.

Particle Size Measurements

Figure 4A:
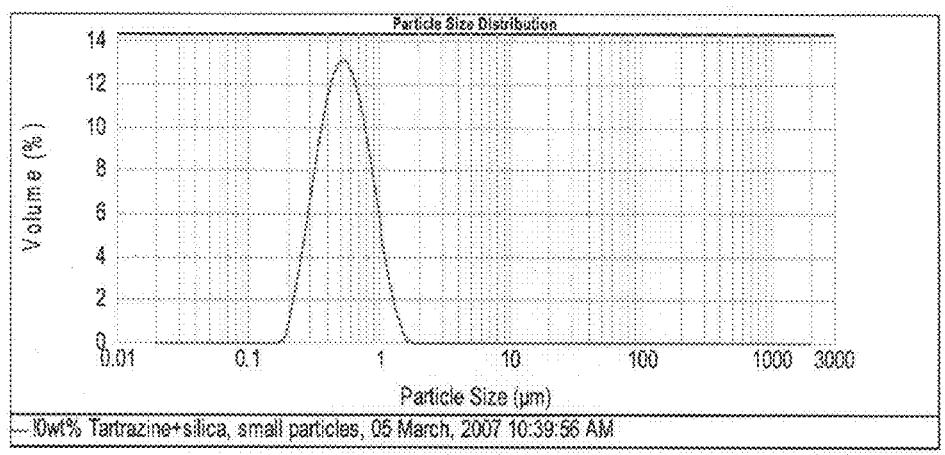
FIG. 4a is a size distribution chart for encapsulated F&DC Yellow 5 particles made according to Example 1.

The size of the resulting particles was measured using a Malvern Master Sizer 2000 apparatus, which measures particle size via light scattering The particle size distribution is shown in the FIG. 4a, in which d(0.1): 0.308 µm (10% of the particles have a size lower than the volume averaged value given)

d(0.5): 0.539 µm (50% of the particles have a size lower than the volume averaged value given)

d(0.9): 0.953 µm (90% of the particles have a size lower than the volume averaged value given)

Example 2

Preparation of Silica loaded with Amaranth (Acid Red No. 27)

This red dye is soluble in water but it is not soluble in ethanol. It was not necessary to ion-exchange the aqueous solution (as was done for Tartrazine in Example 1), however, as it did not flocculate when it was blended with the TEOS mixture. Also, even though the dye was insoluble in ethanol, it was still possible to use it directly by increasing the water proportion in the aerosol mixture.

Sample Preparation

Figure 4B:
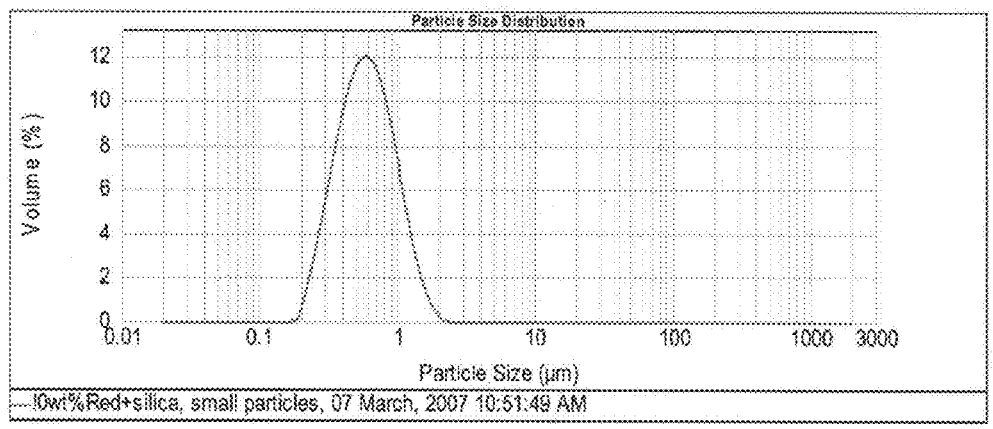
FIG. 4b is a size distribution chart for encapsulated Acid Red No. 27 particles made according to Example 2.

Two batches of coloured silica were prepared using 10.4 g TEOS, 5.4 g of HCl of pH 2 and 12.0 g of ethanol. The components were mixed together and the mixture was left stirring for 30 minutes. Theoretically, the mixture would give 3 g of silica after the aerosolisation. Thus, the calculation of the amount of Amaranth solution (obtained from Sigma has catalogue number A1016-100G (CAS#915-67-3)) to add was based on this amount of silica. This was as follows: 0.3 g of Amaranth powder plus 10.0 g of HCl (pH 2). The two mixtures were mixed together and left to stir for 10 minutes. The mixture was subsequently spray dried, heated, washed, the particles separated and size measured as in example 1. The particle size results are shown in FIG. 4b, and:

d(0.1): 0.322 µm
d(0.5): 0.592 µm
d(0.9): 1.130 µm

Example 3

Preparation of Silica loaded with Erioglaucine (FD & C Blue No. 1)

This blue dye is soluble in water and ethanol and it was not necessary to ion exchange the solution.

Sample Preparation

Figure 4C:
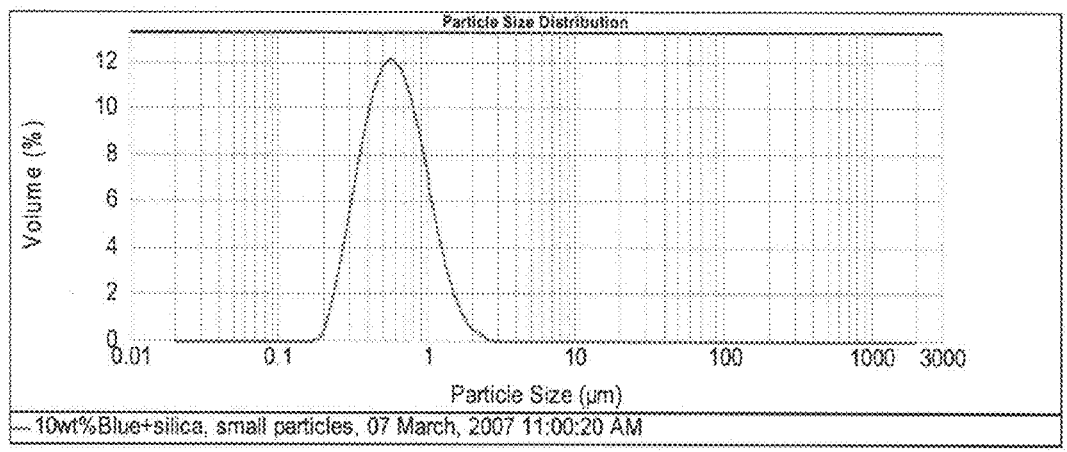
FIG. 4c is a size distribution chart for encapsulated F&DC Blue No. 1 particles made according to Example 3.

Two batches of coloured silica were prepared each using 10.4 g TEOS, 5.4 g HCl (pH2) and 8.0 g of ethanol. The components were mixed together and the mixture was left under stirring for 30 minutes. Theoretically, the mixture would give 3 g of silica after the aerosolisation. Thus, the calculation of the amount of Erioglaucine solution to add was based on this amount of silica. This was as follows: 0.3 g of Erioglaucine powder (obtained from Sigma/Aldrich, catalogue# 861146-25G (CAS#3844-45-9)) plus 2.0 g of HCl (pH 2) in 3 g ethanol. The two mixtures were mixed together and left to stir for 10 minutes. The mixture was subsequently spray dried, heated, washed, the particles separated and size measured as in example 1. The particle size results are shown in FIG. 4c, and:

d(0.1): 0.327 µm
d(0.5): 0.59 µm
d(0.9): 1.130 µm

Example 4

Dye Release/Leakage Experiments

Example 4A

For the products of each of Examples 1, 2 and 3, 0.2 g of the particles loaded with dye were placed into a centrifuge tube and 10 ml of a water/propanol (1:1) mixture was added. The tube was shaken for two minutes and centrifuged. The supernatant fluid was separated from the sediment and collected in a bottle. This operation was repeated five times. The supernatant fluid from all five extractions was mixed and analysed using a UV spectrometer The results are provided in the following table (3).

TABLE 3

| Wash number | Release Yellow, wt % | Release Red, wt % | Release Blue, wt % |
|---|---|---|---|
| 1 | 0.25 | 0.36 | 0.1299 |
| 2 | 0 | 0.027 | 0.0196 |
| 3 | 0 | 0 | 0.0091 |
| 4 | 0 | 0 | 0 |
| 5 | 0 | 0 | 0 |
| Sum over five washes | 0.25 | 0.387 | 0.1586 |

The results show that the release of the dyes into the water/propanol mixture was extremely low.

Example 4B

Figure 5:
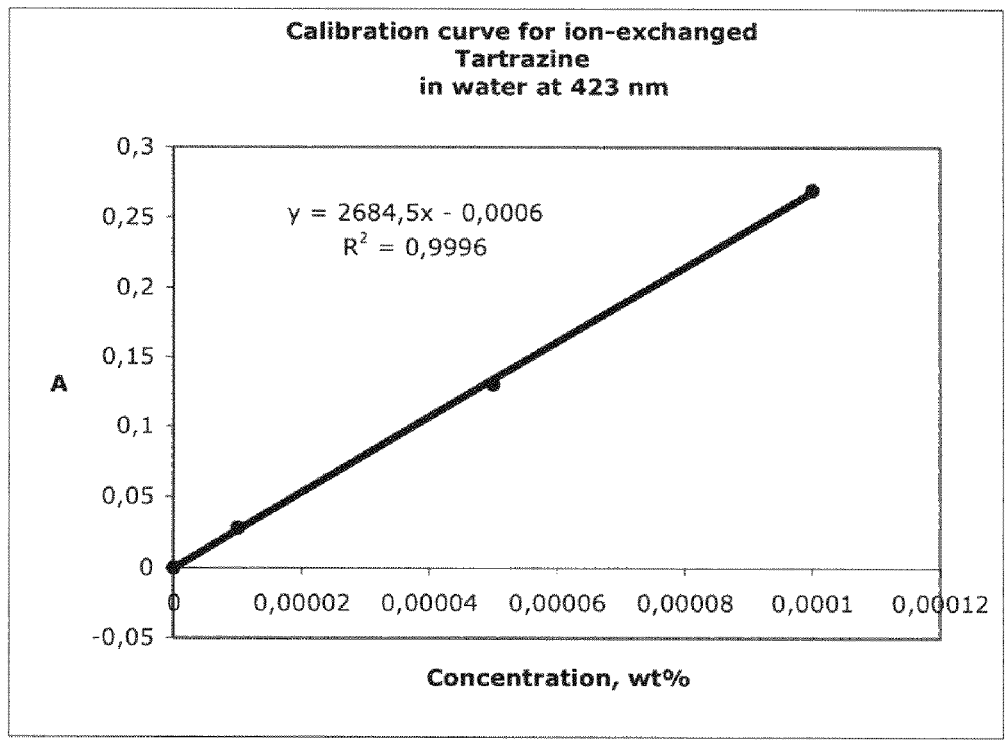
FIG. 5 is the calibration for ion-exchanged Tartrazine in water at 423 nm.

The leakage of Tartrazine from silica loaded with different amounts of dye was investigated as follows. In turn, 1 g of particles loaded with 1%, 5%, 10%, 12% and 15% respectively of Tartrazine was placed into a bottle and 100 g of water was added. The mixture was left under stirring for 3 hours, after which time, a 5 ml portion was extracted from every bottle using a syringe. This portion was filtered with a membrane filter (0.45 μm) and analyzed in an UV-VIS spectrophotometer. The leakage in wt % was calculated for every sample with help of the calibration curve presented as FIG. 5, which shows the calibration for ion-exchanged Tartrazine in water at 423 nm.

The results are presented in the following table (4).

TABLE 4

| Tartrazine Concentration (wt %) | Leakage (wt %) |
|---|---|
| 1 | 0.044 |
| 5 | 0.0528 |
| 10 | 0.155 |
| 12 | 0.727 |
| 15 | 5.37 |

Figure 6:
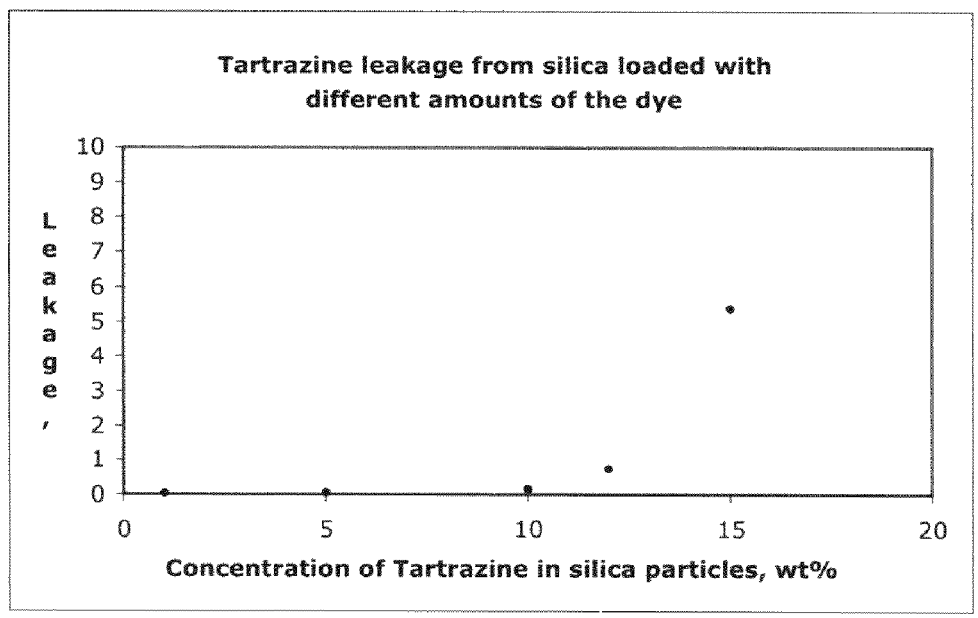
FIG. 6 shows the tartrazine leakage obtained in Example 4B.

These results are presented in FIG. 6, and show that dye leakage, in the case of Tartrazine-loaded particles, substantially increases at greater than 12 wt % Tartrazine concentration within the particles.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for the preparation of amorphous particles comprising a homogeneous distribution of one or more dyes encapsulated by an amorphous, siliceous encapsulating agent, the process comprising:
    (a) providing a precursor of the encapsulating agent in liquid form;
    (b) providing the one or more dyes in liquid form;
    (c) mixing the liquid forms;
    (d) aerosolizing the mixture to form droplets comprising the one or more dyes and encapsulating agent; and
    (e) heating the droplets to form the particles comprising the one or more dyes encapsulated by the siliceous encapsulating agent;
    wherein at least one of the liquid forms provided is aqueous and the aqueous liquid form is acidic;
    wherein the dye is homogeneously dispersed throughout the amorpohous particles; and wherein dye leakage is less than 5% weight of the total amount of dye incorporated into the particle.

2. The process according to claim 1, wherein the precursor of the siliceous encapsulating agent is an organic source of silica.

3. The process according to claim 2, wherein the source of silica is tetraethylorthosilicate.

4. The process according to claim 2, wherein the precursor of the siliceous encapsulating agent is dissolved in a solvent.

5. The process according to claim 1, wherein each dye is cationic.

6. The process according to claim 1, wherein each dye is selected from the group consisting of azo dyes, indigoid dyes, triarylmethane dyes, anthraquinone dyes, xanthine dyes, natural dyes and derivatives, lakes, composites and mixtures thereof.

7. The process according to claim 1, wherein the dye is provided in the form of an acidic, aqueous solution.

8. The process according to claim 1, wherein the heating step (e) is undertaken at a temperature from about 100° C. to about 300° C.

9. The process according to claim 1, comprising the additional step of:
    (f) washing the particles resulting from step (e).

10. The process according to claim 2, wherein the precursor of the siliceous encapsulating agent is selected from the group consisting of tetramethylorthosilicate, tetraethylorthosilicate, tetrapropylorthosilicate, tetraisopropylorthosilicate, tetrabutylorthosilicate, silicic acid, functionalised silica precursors and mixtures thereof.

* * * * *